United States Patent
Lokhandwala et al.

(10) Patent No.: US 9,221,730 B2
(45) Date of Patent: Dec. 29, 2015

(54) FUEL GAS CONDITIONING PROCESS USING GLASSY POLYMER MEMBRANES

(71) Applicants: Kaaeid A. Lokhandwala, Fremont, CA (US); Maliha Williamson, Antioch, CA (US); Sachin Joshi, Mountain View, CA (US)

(72) Inventors: Kaaeid A. Lokhandwala, Fremont, CA (US); Maliha Williamson, Antioch, CA (US); Sachin Joshi, Mountain View, CA (US)

(73) Assignee: Membrane Technology and Research, Inc., Newark, CA (US)

(*) Notice: Subject to any disclaimer, the term of this patent is extended or adjusted under 35 U.S.C. 154(b) by 0 days.

(21) Appl. No.: 14/132,655

(22) Filed: Dec. 18, 2013

(65) Prior Publication Data
US 2014/0107388 A1    Apr. 17, 2014

Related U.S. Application Data

(63) Continuation-in-part of application No. 13/182,106, filed on Jul. 13, 2011, now abandoned.

(51) Int. Cl.
*B01D 53/22* (2006.01)
*C07C 7/144* (2006.01)
*C10L 3/10* (2006.01)

(52) U.S. Cl.
CPC .............. *C07C 7/144* (2013.01); *B01D 53/228* (2013.01); *C10L 3/101* (2013.01); *B01D 2256/245* (2013.01); *B01D 2257/7022* (2013.01)

(58) Field of Classification Search
CPC ............. B01D 53/22; B01D 2256/245; B01D 2257/7025; B01D 53/228; B01D 2257/7022; C07C 7/144; C10L 3/101
USPC ............ 95/45, 50; 96/4, 14; 62/617; 585/818
See application file for complete search history.

(56) References Cited

U.S. PATENT DOCUMENTS

| | | | |
|---|---|---|---|
| 4,370,150 A * | 1/1983 | Fenstermaker | 95/50 |
| 4,842,718 A * | 6/1989 | Luteijn et al. | 95/50 |
| 4,857,078 A | 8/1989 | Watler | |
| 4,963,165 A | 10/1990 | Blume et al. | |
| 5,089,033 A | 2/1992 | Wijmans | |
| 5,199,962 A | 4/1993 | Wijmans | |
| 5,205,843 A | 4/1993 | Kaschemekat et al. | |
| 5,281,255 A | 1/1994 | Toy et al. | |
| 5,352,272 A | 10/1994 | Moll et al. | |
| 5,374,300 A | 12/1994 | Kaschemekat et al. | |
| 5,501,722 A | 3/1996 | Toy et al. | |
| 5,762,685 A | 6/1998 | Baker et al. | |
| 6,053,965 A | 4/2000 | Lokhandwala | |
| 6,361,582 B1 * | 3/2002 | Pinnau et al. | 95/50 |
| 6,723,152 B2 * | 4/2004 | Bikson et al. | 95/45 |
| 6,923,846 B2 * | 8/2005 | Nelson et al. | 95/45 |
| 2004/0168570 A1 * | 9/2004 | Franek | 95/50 |
| 2014/0165829 A1 * | 6/2014 | Sharma et al. | 95/50 |

FOREIGN PATENT DOCUMENTS

| | | | | |
|---|---|---|---|---|
| DE | 10 2008 004077 A1 * | 7/2009 | | C10L 3/10 |
| DE | 102008004077 A1 | 7/2009 | | |

* cited by examiner

*Primary Examiner* — Jason M Greene
(74) *Attorney, Agent, or Firm* — Timothy A. Hott; Janet Farrant

(57) ABSTRACT

Disclosed herein is a process for conditioning natural gas containing $C_{3+}$ hydrocarbons, so that it can be used as combustion fuel to run gas-powered equipment, including gas engines and turbine-driven compressors, in the gas field or the gas processing plant. The claimed process use glassy polymeric membranes that are preferentially permeable to methane over $C_{2+}$ hydrocarbons to produce a partially purified methane stream. The process operates at a stage cut of at least about 5%.

15 Claims, 4 Drawing Sheets

(not in accordance with invention)

FUEL GAS CONDITIONING PROCESS USING GLASSY POLYMER MEMBRANES

This application is a continuation-in-part of U.S. application Ser. No. 13/182,106 filed on Jul. 13, 2011, the disclosure of which is hereby incorporated by reference in its entirety.

FIELD OF THE INVENTION

The invention relates to the upgrading of raw natural gas to run gas engines and turbines in the activity of producing oil and natural gas. More particularly, the invention relates to the use of a glassy polymeric separation membrane to achieve such upgrading.

BACKGROUND OF THE INVENTION

Natural gas is the most important fuel gas in the United States and provides more than one-fifth of all the primary energy used in the United States, Natural gas is also used extensively as a basic raw material in the petrochemical and other chemical process industries. The composition of natural gas varies widely from field to field. For example, a raw gas stream may contain as much as 95% methane, with only minor amounts of other hydrocarbons, nitrogen, carbon dioxide, hydrogen sulfide, or water vapor. On the other hand, streams that contain relatively large proportions of heavier hydrocarbons and/or other contaminants are common. Before the raw gas can be sent to the supply pipeline, it must usually be treated to remove at least one of these contaminants.

As it travels from the wellhead to the processing plant and, ultimately, to the supply pipeline, gas may pass through compressors or other field equipment. These units require power, and it is desirable to run them using gas engines fired by natural gas from the field. Since the gas has not yet been brought to specification, however, this practice may expose the engine to fuel that is of overly high BTU value, low methane number, or corrosive.

In the gas processing plant itself, heavy hydrocarbons are often removed by condensation. Such a method is impractical in the field, however, because sources of external cooling or refrigeration are not available. Furthermore, cooling of the raw gas, which still contains substantial quantities of water vapor, is likely to bring the gas to a pressure temperature composition condition under which hydrates can begin to crystallize, thereby clogging the condensation equipment and preventing gas flow.

That membranes can separate $C_{2+}$ hydrocarbons from gas mixtures, such as natural gas, is known, for example, from U.S. Pat. Nos. 4,857,078; 5,281,255; and 5,501,722. Separation of acid gases from other gases is taught, for example, in U.S. Pat. No. 4,963,165. It has also been recognized that condensation and membrane separation may be combined, as is shown in U.S. Pat. Nos. 5,089,033; 5,199,962; 5,205,843; and 5,374,300.

It is also known to operate membrane systems at reduced temperatures by deliberately cooling the incoming feed stream, as is taught in U.S. Pat. No. 5,352,272, and to use the Joule-Thomson cooling produced by transmembrane permeation to facilitate upstream condensation, as is taught in U.S. Pat. No. 5,762,635.

U.S. PG Pub. No. 2004/0168570, to Franek, discloses an apparatus and process for separating purified methane from hydrocarbons higher than $C_1$ in a feed gas mixture using a membrane. The membrane has a higher permeability for methane compared to other higher hydrocarbons, resulting in a permeate stream of highly pure methane essentially void of higher hydrocarbons.

German Patent Application Publication DE 10 2008 004077A1 (English Translation), to König (MAN Diesel SE), discloses a method and apparatus using membrane separation for the treatment of natural gas for use in a gas engine. An objective of the invention is to improve the fuel gas quality by increasing the methane number, thereby reducing common knocking problems found in poor quality fuel. The fuel to be treated has a methane number of at most 90, especially at most 80, and preferably at most 70.

The problem of upgrading raw gas in the field, such as to sweeten sour gas, is addressed specifically in U.S. Pat. No. 4,370,050, to Fenstermaker. In this patent, Fenstermaker teaches a process that uses a membrane, selective for hydrogen sulfide and/or heavier hydrocarbons over methane, to treat a side stream of raw gas. The process produces a membrane residue stream of quality appropriate for engine fuel. The contaminants pass preferentially through the membrane to form a low-pressure permeate stream, which is returned to the main gas line upstream of the field compressor. Such a process relies on there being sufficient compressor capacity available to handle the return stream that is recycled to the compressor inlet.

However, if the raw gas requires more than a minor adjustment in composition, the proportion of gas that has to be recycled to the compressor may be comparatively large. For example, to upgrade the methane content from 70% to 80%, or from 80% to 90%, may require as much as 50% of the gas being treated by the membrane to be returned for recompression. If the gas is more heavily contaminated, such as containing hydrogen sulfide at the percent level, for example, as is not uncommon, the proportion returned on the low pressure side may be even higher, such as 60% or more. As well as diverting compressor capacity, this makes for an inefficient use of fuel, since fuel gas created by the membrane is used in part to recompress the fuel reject stream.

In commonly owned U.S. Pat. No. 6,053,965 (hereinafter referred to as "the '965 patent"), we disclosed a membrane-based process for conditioning natural gas containing $C_{3+}$ hydrocarbons and/or acid gas, so that it can be used as combustion fuel to run gas-powered equipment, including compressors, in the gas field or a gas processing plant. The method disclosed in the '965 patent differs from previous membrane-based processes available for field engine fuel conditioning in that it creates substantially lesser quantities of low-pressure gas per unit volume of fuel gins produced. This is achieved by using a membrane separation step in conjunction with a condensation step under pressure, for which the cooling is provided by the membrane separation step, and by balancing the amount of contaminants removed in the condensation and membrane separation steps.

According to the general process disclosed in the '965 patent, a portion of gas from a high-pressure gas stream is withdrawn, then cooled by passing the portion through a heat-exchange step in heat-exchanging relationship against a membrane residue stream. The portion is then separated into a liquid phase comprising $C_{3+}$ hydrocarbons and a gas phase depleted in $C_{3+}$ hydrocarbons. The gas phase is then passed across the feed side of a membrane unit containing a membrane selective for $C_{3+}$ hydrocarbons over methane. A $C_{3+}$-depleted membrane residue stream is then withdrawn from the feed side and passed back to the heat exchange step. A $C_{3+}$-enriched permeate stream is withdrawn from the permeate side. The membrane residue stream may optionally be used as combustion fuel for a prime mover.

A schematic drawing of a basic embodiment of the process disclosed in the '965 patent is shown in FIG. 1. Referring to this figure, stream 101, which is the stream to be treated by the process, is withdrawn from high-pressure natural gas stream, 100. Stream 101 passes into heat exchanger, 102, where gas stream 101 is brought into heat-exchanging relationship with $C_{3+}$-depleted membrane residue stream, 109.

Cooling of residue stream 109 results in the formation of a two-phase mixture, 103, which exits heat exchanger, 102, and passes into phase separator, 104. The liquid phase, containing liquefied hydrocarbons, water, and dissolved gases, is withdrawn as condensate stream, 105.

The high-pressure gas phase from the separator stream, 106, passes to the membrane separation unit, 107, where it is separated into contaminant-enriched permeate stream, 108, and contaminant-depleted residue stream, 109. Stream 108 is withdrawn from the membrane permeate side and may optionally be reintroduced into the main gas flow on the low-pressure inlet side of the pipeline compressor, if any. Depending on the relative volume flow rates of streams 108 and 100, as much as 20-30% or more of the compressor capacity may be used to recompress the gas that is returned to the local pipeline.

Residue stream 109 is withdrawn from the membrane feed side and passes to heat exchanger 102, whence it emerges as conditioned fuel gas stream, 110.

The process of the '965 patent requires the conditioned membrane residue stream to be decompressed before being used as fuel. Decompression results in cooling of the gas to a low temperature, and heating the gas to avoid hydrate formation adds energy-consuming inefficiency to the process.

Thus, although the processes of the '965 patent and the other patents above represent useful improvements over then prior art processes, there remains a need for a process that provides an improved fuel gas for field use, but that is more efficient in terms of compression requirements and overall energy efficiency.

SUMMARY OF THE INVENTION

The invention is a process for conditioning natural gas containing $C_{2+}$ hydrocarbons and/or acid gas, so that it can be used as combustion fuel to run gas-powered equipment, including compressors, such as at the wellhead or elsewhere in the field upstream of the gas processing plant. The process is carried out on at least part of a natural gas stream that is at high pressure, typically, although not necessarily, after it has passed through a compressor.

The process disclosed in the '965 patent utilizes rubbery polymeric membranes that are preferentially permeable to $C_{2+}$ hydrocarbons over methane. The resulting heavy hydrocarbon-enriched permeate stream is recycled back to the compressor suction. This process relies on the differential pressure between the suction and exhaust sides of the compressor to effect the membrane-based gas separation. The conditioned, high-pressure residue stream must be throttled down to fuel header pressure prior to being used as a combustion fuel in a gas engine, for example.

The present invention essentially reverses the approach taken in the '965 patent by using glassy polymeric membranes that are preferentially permeable to methane over $C_{2+}$ hydrocarbons. The heavy hydrocarbon-depleted permeate at lower pressure is now the product and can be muted directly to the fuel header. The high-pressure residue stream can be returned to the pipeline at an appropriate pressure point, thereby reducing or avoiding the need for the return stream to occupy compressor capacity. For example, the residue stream can be returned to the pipeline either upstream or downstream of additional processing equipment (which may be a glycol dehydrator, a cooler, a heater, for example, and not by way of limitation).

By avoiding or at least substantially reducing recycle through the compressor, the parasitic loss is correspondingly reduced or eliminated. Furthermore, we found that the fuel gas product quality, in terms of BTU/sef, is about the same with the process of the present invention than with prior art processes, but does not require the additional compression capacity that is required with the process disclosed in the '965 patent.

Accordingly, disclosed herein is a process for conditioning a portion of a gas stream, the gas stream comprising at least methane and $C_{2+}$ hydrocarbons. In its most basic embodiment, the process of the invention comprises the following steps:

(a) withdrawing the portion from the gas stream;
(b) providing a membrane unit having a feed side, a permeate side, and a residue side, and containing a membrane selective for methane over $C_{2+}$ hydrocarbons;
(c) passing the portion as a feed stream across the feed side under conditions in which transmembrane permeation occurs;
(d) withdrawing from the residue side a membrane residue stream;
(e) withdrawing from the permeate side a membrane permeate stream depleted in $C_{2+}$ hydrocarbons compared with the feed stream; and
(f) routing the membrane permeate stream as a portion of a fuel stream to a fuel user, wherein the process operates at a stage cut of at least 5%.

Prior to being routed to the membrane separation step, the portion is typically passed to a pre-treatment step, which may be (for example and not by way of limitation) a filtration step and/or a heating step. If the pre-treatment step is a filtration step, filtration is typically performed using apparatus selected from the group consisting of a single-stage coalescing filter, a two-stage coalescing filter, a carbon bed, a molecular sieve bed, a refrigeration or cooling source, and combinations thereof. All of these apparatus are well-known in the art. It is particularly preferred that the apparatus is a coalescing filter.

The membrane residue stream is typically routed back to the high-pressure gas stream at an appropriate pressure point either upstream or downstream of where the portion is withdrawn. Alternatively, the membrane residue stream can be processed to recover $C_{2+}$ hydrocarbon liquids.

As used herein, the term "fuel user" refers to any apparatus or equipment that is configured to use a methane-containing gas as fuel to generate power. The fuel user is typically a gas engine or other device used to generate power or drive a compressor, but may alternatively be a generator set or a boiler. The gas stream being treated using the process of the invention is typically a high-pressure gas stream created by a compressor driven by a gas engine, and step (f) typically involves using the membrane permeate stream as fuel for the gas engine. The membrane permeate stream may be routed to the fuel user through a pressure control valve at an appropriate pressure point.

The process is preferably operated in such a manner as to maintain the hydrocarbon dewpoint on the feed side of the membrane below the operating temperature of the membrane modules to avoid condensation of liquid hydrocarbons directly on the membrane surface. This can be achieved by heating the feed gas or by controlling the stage cut, or both.

The process is preferably operated at a stage cut of at least 5%, depending on the specifics of the gas to be treated. Operation at lower stage cuts than 5% should be avoided, as this is inefficient and may overprocess the gas to the point that the Btu value is too low, as explained further below.

Operation at very high stage cuts, such as above 75%, should also be avoided, as this is likely to produce substantial elevation of the hydrocarbon dewpoint on the feed side, to the point that hydrocarbon condensation in the membrane modules cannot be avoided even by heating the feed stream.

Membranes for use in the process of the invention may comprise any polymer that will preferentially permeate methane over $C_{2+}$ hydrocarbons. Preferred membrane materials are glassy polymers, such as, for example and without limitation, polyamides, polyimides, polysulfones, polyvinyl alcohol, polypropylene oxide, cellulose derivatives, polyvinylidene fluoride, and polymers having repeating units of fluorinated dioxoles, fluorinated dioxolanes, and fluorinated cyclically polymerizable alkyl ethers.

Particularly preferred membranes for use in the process of the invention have selective layers made from a hydrophobic fluorinated glassy polymer or copolymer. This polymer determines the membrane selectivity.

The process removes $C_{2+}$ hydrocarbons and/or acid gas from the raw gas, thereby enabling fuel users such as field engines, turbines, and the like to be run using gas that would otherwise be too rich in heavy hydrocarbons or too contaminated with acid gas. Thus, the process provides a cleaner-burning fuel and reduces engine problems or damage associated with knocking.

Although it is described herein principally as it relates to conditioning gas for use as engine or turbine fuel, it will be apparent to those of skill in the art that the process could be applied to lighten, sweeten, or dry high-pressure gas streams for any purpose where control of the quantity of low-pressure gas produced is desired. The treatment of high-pressure gas streams consistent with the teachings herein is within the scope of the invention, whether applied to preparation of engine fuel or for any other purpose.

It is to be understood that the above summary and the following detailed description are intended to explain and illustrate the invention without restricting its scope.

DETAILED DESCRIPTION OF THE INVENTION

Figure 1:
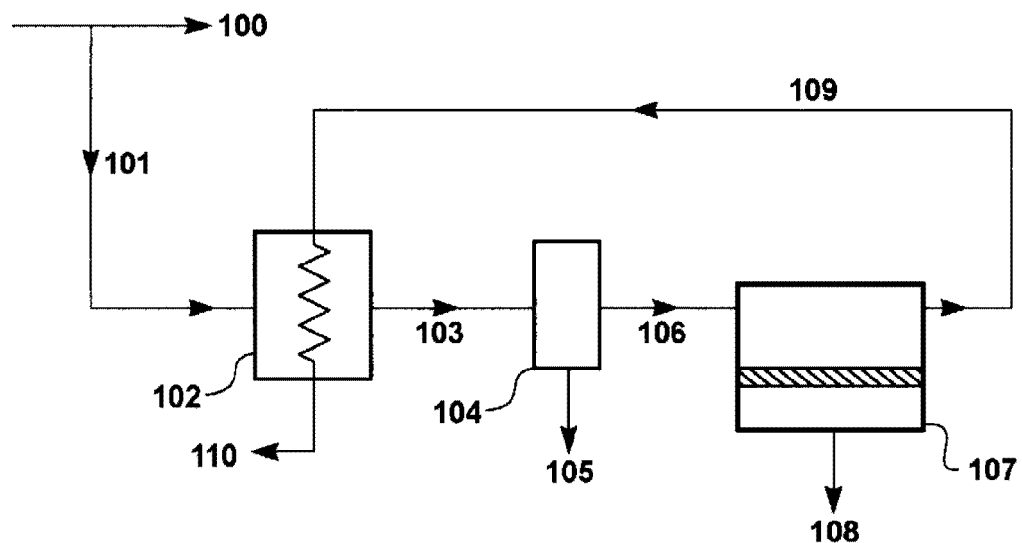
FIG. 1 is a schematic drawing of the fuel gas conditioning process taught in commonly owned U.S. Pat. No. 6,053,965. This patent teaches a process for conditioning fuel gas using rubbery polymer membranes (not in accordance with the present invention).

The terms "$C_{2+}$ hydrocarbon" and "heavier hydrocarbon" mean a hydrocarbon having at least two carbon atoms.

The term "fuel user" refers to any apparatus or equipment that is configured to use a methane-containing gas as fuel to generate power.

The term "gas" as used herein means a gas or a vapor.

The term "high-pressure gas stream" means a gas stream at a pressure of at least 100 psia.

The terms "lighter" and "leaner" mean reduced in $C_{2+}$ hydrocarbons content.

The term "membrane array" means a set of membrane modules or banks of modules connected in multi-step arrangement, multi-stage arrangement, or mixtures or combinations of these.

The term "product permeate stream" means the permeate stream exiting a membrane array when the membrane separation process is complete. This stream may be derived from one membrane bank, or may be the pooled permeate streams from several membrane banks.

The term "product residue stream" means the residue stream exiting a membrane array when the membrane separation process is complete. This stream may be derived from one membrane bank, or may be the pooled residue streams from several membrane banks.

The term "sweeter" means reduced in hydrogen sulfide content.

The terms "two-step" and "multi-step" as used herein mean an arrangement of membrane modules or banks of membrane modules connected together such that the residue stream from one module or bank of modules becomes the feed stream for the next.

The terms "two-stage" and "multi-stage" as used herein mean an arrangement of membrane modules or banks of membrane modules connected together such that the permeate stream from one module or bank of modules becomes the feed stream for the next.

The term "stage cut" as used herein means the ratio of permeate flow to feed flow for a membrane unit, in other words, the volume fraction of the feed gas that permeates the membrane.

Percentages herein are by volume unless otherwise stated.

The invention is an improved process for conditioning natural gas containing $C_{2+}$ hydrocarbons and/or acid gas, so that it can be used as fuel to run engines or turbines in the gas field or elsewhere as appropriate, or for any other purpose.

In general, engines can operate on a poorer quality of gas than is needed to meet supply pipeline specification. For example, pipeline specification is typically no more than 4 ppm hydrogen sulfide, no more than 1-3% carbon dioxide, no more than about 140 ppm water vapor, and a hydrocarbon dew-point below 0° C. at 1,000 psia, which translates roughly to a total $C_{2+}$ hydrocarbon content of no more than about 5%, of which no more than about 1-2 is $C_{4+}$ hydrocarbons. In contrast, a field engine may be able to operate satisfactorily on a gas that contains, for example, as much as 1,000 ppm of hydrogen sulfide and/or 15 total $C_{2+}$ hydrocarbons.

Nevertheless, many or most raw streams do not meet this specification. The streams that may be treated by the process of the invention are diverse and include, without limitation, those that contain excess $C_{2+}$ hydrocarbons, large amounts of acid gases, specifically hydrogen sulfide or carbon dioxide, nitrogen, and/or large amounts of water vapor.

The process is especially useful for treating gas with relatively high $C_{2+}$ hydrocarbon content. This content is typically a mix of $C_2$-$C_{10}$ components. By relatively high, we mean a total $C_{2+}$ hydrocarbon content of up to 20 vol %, or even more. The methane content of the raw gas may be any value, but commonly will be in the range 50-99 vol % methane, and most typically will be in the range 60-95 vol % methane.

Traditionally, rubbery polymeric membranes have been used to remove heavy ($C_{2+}$) hydrocarbons from natural gas streams. Herein, we propose the use of glassy polymer membranes to remove methane from raw gas to meet engine or turbine fuel specifications. The invention involves passing a stream of the raw gas across a methane-selective membrane, which is typically a glassy polymer membrane, and is most preferably a perfluorinated polymer membrane.

Figure 4:
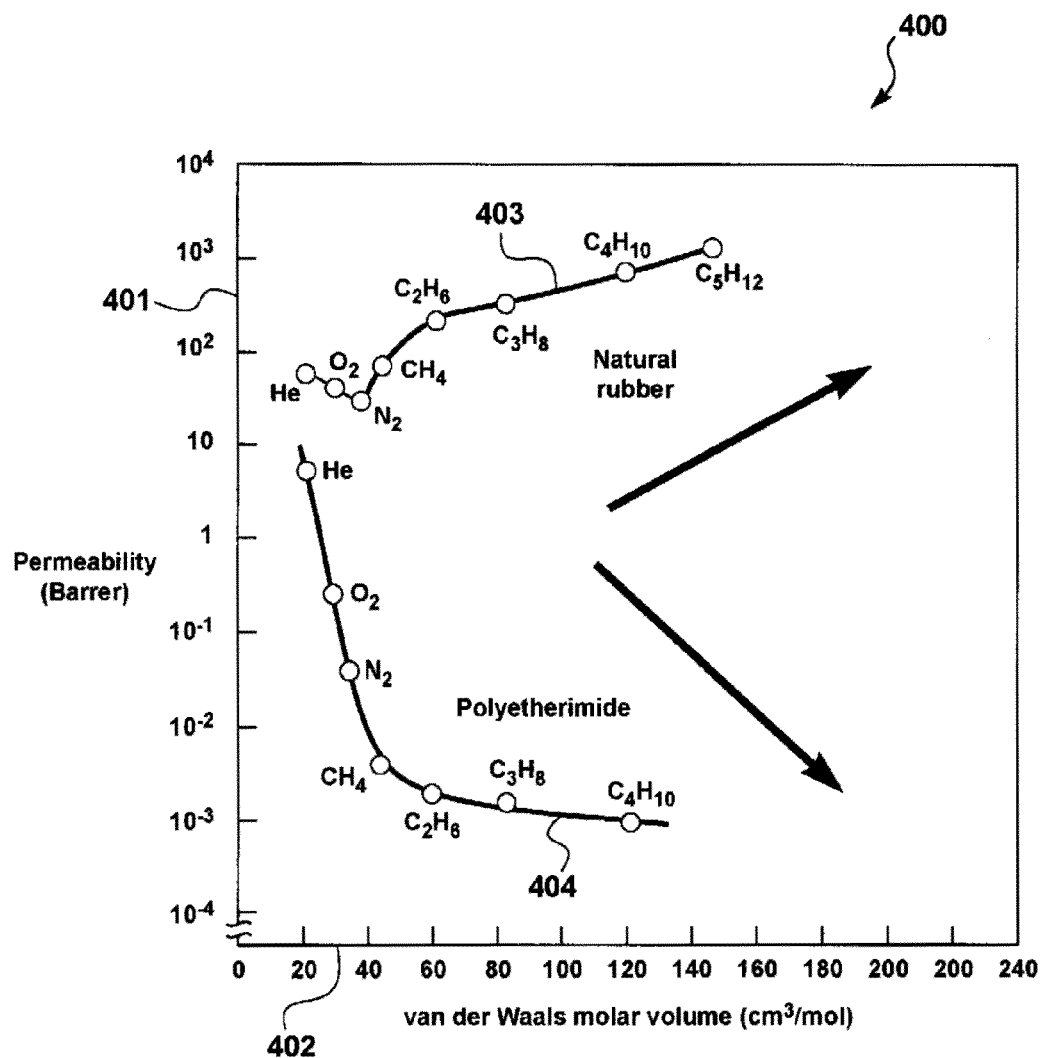
FIG. 4 is a plot showing permeability (in barrer) for various gases as a function of van der Waals molar volume (in cm³/mol) through natural rubber membranes and glassy polyetherimide membranes.

The mechanisms for permeation of various molecules through rubbery membranes and glassy membranes are quite different from each other. FIG. 4 is a plot, 400, showing permeability (in barrer), 401, for various gases as a function of van der Waals molar volume (in cm$^3$/mol), 402, through natural rubber membranes, 403, and glassy polyetherimide membranes, 404.

With rubbery membranes, permeation is solubility selective, with the controlling mechanism being the solubility coefficient, with condensability also being a factor. With glassy membranes, permeation is size-selective, with the controlling, mechanism being the diffusion coefficients of the various molecules.

Figure 2:
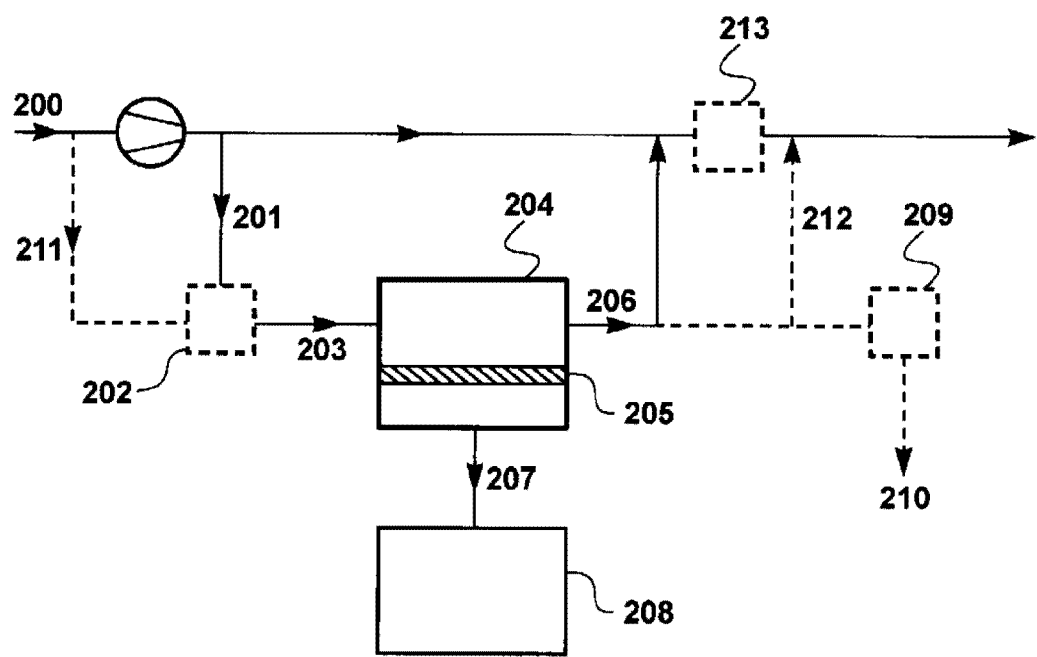
FIG. 2 is a schematic drawing of a basic embodiment of the present invention, which utilizes glassy polymer membranes to condition fuel gas.

Referring to the figures, the invention in its most basic form is shown in FIG. 2, which is a schematic drawing of a process for conditioning a portion of a gas stream, 200, where the gas stream comprises methane and $C_{2+}$ hydrocarbons.

Referring to FIG. 2, the portion may be withdrawn from the gas stream 200 either post-compression, 201, or pre-compression, as indicated by broken line, 211. The withdrawn portion (201 or 211) typically comprises about 0.1 to about 100 vol %, and preferably, between about 1 to about 100 vol %, of gas stream 200.

The withdrawn portion is optionally but typically passed through a pre-treatment step, 202, which may be a filtration step and/or a heating step, for example and not by way of limitation. If pre-treatment step 202 is a filtration step, filtration is typically performed using a single-stage coalescing filter, a two-stage coalescing filter, a carbon bed, a molecular sieve bed, a refrigeration or cooling source, or combinations thereof. All of these apparatus are well-known in the art. It is particularly preferred that the apparatus comprises a coalescing filter.

A heating step may or may not be required, depending on the gas composition, ambient conditions and the stage cut at which the process is operated, which feature is discussed in more detail below. If heating is used, the temperature of the gas should be raised to a level comfortably (such as 10° C. or 20° C.) above the dewpoint of the residue gas. As a representative, non-limiting example, the gas may be heated to 50 or 60° C.

The resulting stream is passed as a feed stream, 203, to membrane unit, 204, which contains membranes, 205, which are selective for methane over $C_{2+}$ hydrocarbons.

Membranes for use in the process of the invention may comprise any polymer that will preferentially permeate methane over $C_{2+}$ hydrocarbons. Preferred membrane materials are glassy polymers, such as, for example and without limitation, polyamides, polyimides, polysulfones, polyvinyl alcohol, polypropylene oxide, cellulose derivatives, polyvinylidene fluoride, and polymers having repeating units of fluorinated dioxoles, fluorinated dioxolanes, and fluorinated cyclically polymerizable alkyl ethers.

Particularly preferred membranes for use in the process of the invention have selective layers made from a hydrophobic fluorinated glassy polymer or copolymer. This polymer determines the membrane selectivity.

The polymer is characterized by having repeating units of fluorinated, cyclic structure, the fluorinated ring having at least five members, where the fluorinated ring is preferably in the polymer backbone. Preferably, the polymer is formed from a monomer selected from the group consisting of fluorinated dioxoles, fluorinated dioxolanes, and fluorinated cyclically polymerizable alkyl ethers.

The fluorinated polymer is preferably heavily fluorinated, by which we mean having a fluorine:carbon ratio of atoms in the polymer of at least about 1:1. Most preferably, the polymer is perfluorinated.

Particularly preferred materials for the selective layer of the membrane used to carry out the process of the invention are amorphous homopolymers of perfluorinated dioxoles, dioxolanes or cyclic alkyl ethers, or copolymers of these with tetrafluoroethylene. These preferred polymer materials are amorphous glassy materials with glass transition temperatures in the range of 100° C. to 250° C. The exceptional permeation properties of these membranes are derived from their structure. The materials are amorphous, glassy, highly fluorinated and without any ionic groups that would render the membranes hydrophilic or provide an affinity for other polar materials. As a result, they are not swollen to any significant extent by polar solvents, such as ethanol, isopropanol, butanol, acetone, acetic acid, and water. This low sorption, together with the intrinsic resistance to hydrolysis of fluoro polymers, makes these polymers chemically stable.

Specific highly preferred materials include copolymers of tetrafluoroethylene with 2,2,4-trifluoro-5-trifluoromethoxy-1,3-dioxole having the structure:

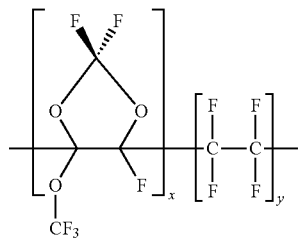

where x and y represent the relative proportions of the dioxole and the tetrafluoroethylene blocks, such that x+y=1.

Such materials are available commercially from Solvay Solexis, Inc., of Thorofare, N.J., under the trade name Hyflon® AD. Different grades are available varying in proportions of the dioxole and tetrafluoroethylene units, with fluorine:carbon ratios of between 1.5 and 2, depending on the mix of repeat units. For example, grade Hyflon® AD 60 contains a 60:40 ratio of dioxole to tetrafluoroethylene units, has a fractional free volume of 0.23 and a glass transition temperature of 121° C., and grade Hyflon®AD 80 contains an 80:20 ratio of dioxole to tetrafluoroethylene units, has a fractional free volume of 0.23 and a glass transition temperature of 134° C.

Other specific highly preferred materials include the set of polyperfluoro (alkenyl vinyl ethers) including polyperfluoro (allyl vinyl ether) and polyperfluoro (butenyl vinyl ether) that are cyclically polymerizable by the formation of repeat units of ether rings with five or six members in the ring.

A particular preferred material of this type has the structure:

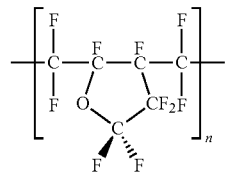

Where n is a positive integer.

This material is available commercially from Asahi Glass Company, of Tokyo, Japan, under the trade name Cytop®.

Cytop® has a fractional free volume of 0.21, a glass transition temperature of 108° C., and a fluorine carbon ratio of 1.7.

A third group of materials that is believed to contain useful selective layer materials under some circumstances is:

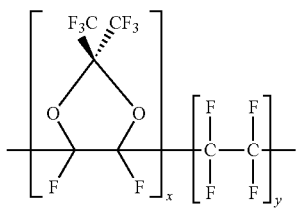

Where x and y represent the relative proportions of the dioxole and the tetrafluoroethylene blocks, such that x+y=1.

Such materials are available commercially from DuPont of Wilmington, Del., under the tradename Teflon® AR. The polymer chosen for the selective layer can be used to form films or membranes by any convenient technique known in the art, and may take diverse forms. The membrane may take the form of a homogeneous film, an integral asymmetric membrane, a multilayer composite membrane, a membrane incorporating a gel or liquid layer or particulates, or any other form known in the art. If super-glassy membranes are used, they may be formed as integral asymmetric or composite membranes.

Because the polymers are glassy and rigid, an unsupported film, tube, or fiber of the polymer is usable as a single-layer membrane. However, single-layer films will normally be too thick to yield acceptable transmembrane flux however, and, in practice, the separation membrane usually comprises a very thin selective layer that forms part of a thicker structure, such as an integral asymmetric membrane or a composite membrane.

The preferred form is a composite membrane. Modern composite membranes typically comprise a highly permeable, but relatively non-selective, support membrane that provides mechanical strength, coated with a thin selective layer of another material that is primarily responsible for the separation properties. Typically, but not necessarily, such a composite membrane is made by solution-casting the support membrane, then solution-coating the selective layer. Preparation techniques for making composite membranes of this type are well known.

The membranes may be manufactured as flat sheets or as fibers and housed in any convenient module form, including spiral-wound modules, plate-and-frame modules, and potted hollow fiber modules. The making of all these types of membranes and modules is well-known in the art. Flat-sheet membranes in spiral-wound modules is the most preferred choice.

Membrane unit 204 may contain a single membrane module or bank of membrane modules or an array of modules. A single-stage membrane separation operation is adequate for many applications. If the permeate stream requires further purification, it may be passed to a second bank of membrane modules for a second processing step. If the residue stream requires further concentration, it may be passed to a second bank of membrane modules for a second-stage treatment. Such multi-stage or multi-step processes, and variants thereof, will be familiar to those of skill in the art, who will appreciate that the membrane separation step may be configured in many possible ways, including single-stage, multi-stage, multi-step, or more complicated arrays of two or more units in serial or cascade arrangements.

Feed stream 203, which is most typically at high pressure, flows across the feed surface of membrane 205. The permeate side of the membrane is maintained at lower pressure to provide a driving force for transmembrane permeation. Methane permeates the membrane preferentially, resulting in contaminant-enriched residue stream, 206, and contaminant-depleted permeate stream, 207. Typically, the feed side is maintained at a pressure within the range of about 30 psig to about 5,000 psig; preferably, within the range of about 50 psig to about 1,500 psig. The permeate side is typically maintained at a pressure within the range of about 1 psig to about 3,000 psig; preferably, within the range of about 1 psig to about 1,000 psig.

As is familiar to those of skill in the art, the separation performance achieved by the membrane depends on such factors as the membrane selectivity, the pressure ratio between feed and permeate sides, and the membrane area. The transmembrane flux depends on the permeability of the membrane material, the pressure difference across the membrane, and the membrane thickness.

In the case of preparation of fuel gas for use in gas field equipment, generally before the gas has undergone treatment at the gas processing plant, we have discovered that a particular feature of the process that must be managed carefully is the stage cut.

As defined above, in a membrane gas separation process, stage cut refers to the percentage of the feed gas that permeates the membrane. Since the membrane is selective in favor of methane over hydrocarbons, operating at a very low stage cut will enable only a few percent of the feed gas to permeate the membrane, resulting in a permeate gas that contains very little, or only traces of, the relatively less permeable $C_{2+}$ hydrocarbons. If the gas contains no other components than hydrocarbons, then, assuming appropriate choices for other operating parameters, this means that the permeate can be high purity methane, with a methane content of 97 vol %, 98 vol % or even higher.

In the gas field, however, the raw gas almost always contains substantial quantities of other contaminants, such as carbon dioxide, nitrogen and water, to all of which the glassy membranes used in the invention will also be selective over $C_{2+}$ hydrocarbons. Thus, the highly $C_{2+}$ hydrocarbon depleted permeate will now be a mix of methane plus nitrogen, carbon dioxide, water vapor or any other gas contaminants that permeate the membrane preferentially compared with the heavier hydrocarbons. As a result, the methane concentration of the permeate may actually be lower than the methane concentration of the feed, and the Btu value of the gas may have become too low for efficient combustion, or at least will have been overprocessed way beyond what is necessary to run field engines. Furthermore the process is inefficient in itself, because almost all of the gas being handled by the membrane modules passes through on the feed side and emerges as residue, so the volume of useful fuel gas produced per unit of gas processed is small.

To avoid the above problems, we prefer to operate at a stage cut of at least 5%, and more preferably at least 8%, or in some circumstances at least 10%, depending on the specific features of the gas to be treated. In this way, a gas that is adequately conditioned for use as field gas fuel can be produced without overprocessing or other inefficiencies.

At the other extreme, operation at very high stage cuts should also be avoided. The higher the stage cut, the larger the volume of conditioned gas produced, since the proportion of gas permeating the membrane is high. However, removal of methane and other gases into the permeate will progressively elevate the $C_{2+}$ hydrocarbon content of the gas remaining on the feed side, with corresponding elevation of the hydrocarbon dewpoint. At a certain stage cut, the hydrocarbon dewpoint, especially of raw gases that are relatively high in initial $C_{2+}$ components, and especially the $C_{4+}$ components, will become so high that hydrocarbon condensation in the membrane modules cannot be avoided without heating the gas or the modules to a point that becomes impractical in the field, or even, depending on the polymers used, at which the membranes start to plasticize.

In light of these considerations, for typical gas compositions we prefer to operate at a stage cut of no higher than about 75%, more preferably no higher than 70%, and most preferably no higher than 65%.

Returning to FIG. 2, a membrane residue stream 206 is withdrawn from the feed side of the membrane unit 204. Membrane residue stream 206 is then typically routed back to high-pressure gas stream 200 at an appropriate pressure point, which may be either upstream or downstream (as shown in the figure) of where portion 201 was withdrawn. For example, the residue stream can be returned to the pipeline either upstream or downstream (indicated by broken line 212) of additional processing equipment, 213 (which may be a glycol dehydrator, a cooler, a heater, for example, and not by way of limitation), to take advantage of pressure differential across the equipment.

In an alternative embodiment, the membrane residue stream is passed through a condenser 209, where it is partially condensed to recover $C_{2+}$ hydrocarbon liquids 210.

A membrane permeate stream, 207, enriched in methane and depleted in $C_{2+}$ hydrocarbons compared to the membrane feed stream 203 is withdrawn from the permeate side of membrane unit 204. The membrane permeate stream 207 is typically routed through a fuel intake (not shown) to a fuel user, 208, which is typically a gas engine or other device used to generate power or drive a compressor, but may alternatively be a generator set or boiler, for example and not by way of limitation.

In terms of methane content, and taking into account the stage cut considerations discussed above, it is preferred that membrane permeate stream 207 has a methane concentration preferably greater than 75 mol %, and usually less than 95 mol %.

Figure 3:
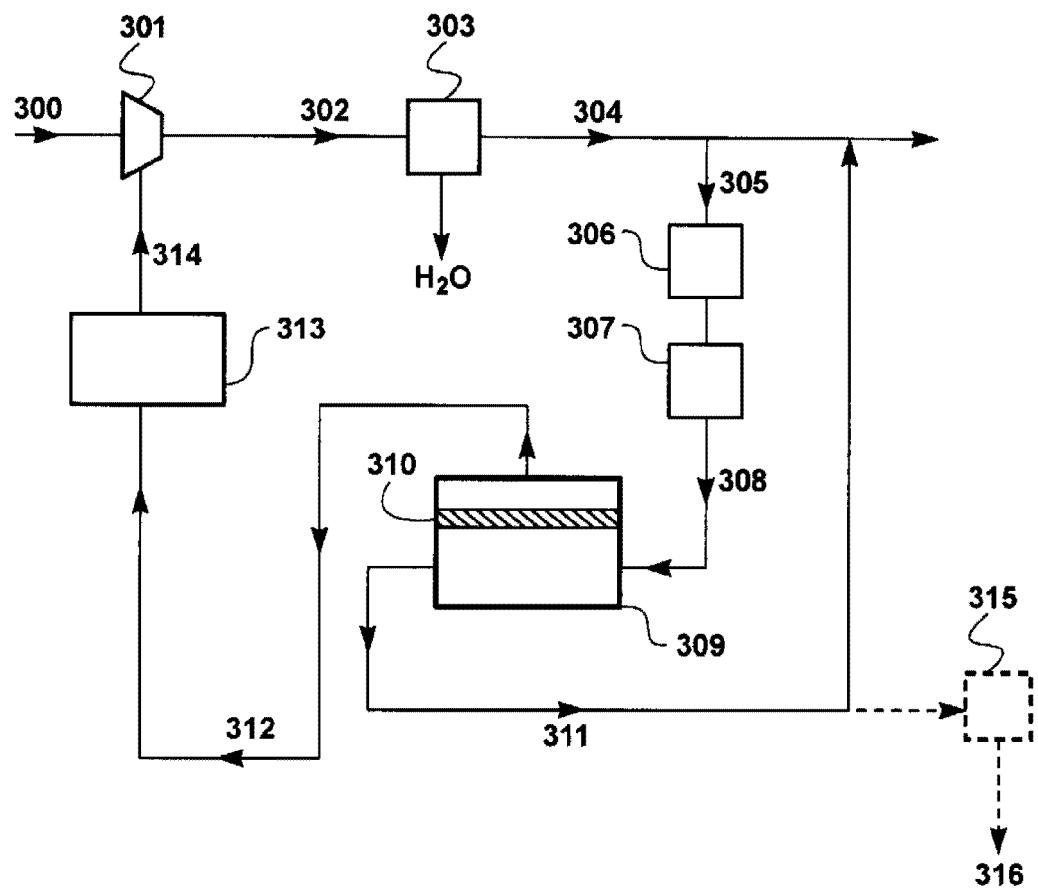
FIG. 3 is a schematic drawing of a preferred embodiment of the present invention.

In certain embodiments of the invention, the gas stream to be conditioned is a high-pressure stream created by a gas engine which uses the membrane permeate stream as fuel. An example of such an embodiment is shown in FIG. 3. Unless explicitly stated otherwise, the considerations and preferences with respect to stage cut and other features of the invention discussed above are the same for the embodiment of FIG. 3 as for the embodiment of FIG. 2.

Referring to FIG. 3, incoming gas stream, 300, comprising methane and $C_{2+}$ hydrocarbons, is compressed to a pressure within the range of about 1 bar to about 300 bar using compressor or compression step or train, 301. Gas engine, 313, provides power, 314, to compressor 301.

Compressed gas stream, 302, is then cooled to a temperature within the range of about 0° C. to about 80° C. in aftercooler, 303. A portion, 305, of cooled gas stream, 304, is then routed to a filtration step, 306, as described above. The filtered stream is passed to a heater, 307, where it is typically heated to a temperature within the range of about 10° C. and about 100° C., then passed as a feed stream, 308, to membrane unit, 309, which contains membranes, 310, which are selective for methane over $C_{2+}$ hydrocarbons, as described above.

A membrane residue stream, 311, is withdrawn from the feed side of the membrane unit, 309, containing membranes having characteristics similar to those already described for membranes 205. Membrane residue stream 311 is then typically routed back to high-pressure gas stream 304 at an appropriate pressure point, which may be either upstream or downstream (as shown in the figure) of where portion 305 was withdrawn.

In an alternative embodiment (indicated by the broken lines in FIG. 3), membrane residue stream 311 is passed through a condenser 315 to recover C hydrocarbon liquids 316.

To avoid process inefficiencies, as well as potential hydrocarbon liquefaction and/or formation of harmful hydrates, the operating preferences expressed already expressed with respect to stage cut and temperature should be observed.

A membrane permeate stream, 312, enriched in methane and depleted in $C_{2+}$ hydrocarbons compared to the membrane feed stream 308 is withdrawn from the permeate side of membrane unit 309. The membrane permeate stream 312 is routed to a fuel user, 313, which is typically a gas engine or other device used to generate power, 314, to drive compressor 301, through a pressure control valve (not shown) at an appropriate pressure point.

EXAMPLES

Calculations were performed to compare the composition of conditioned fuel gas produced by membrane separation using traditional rubbery membranes according to the general process shown in FIG. 1 (and disclosed in U.S. Pat. No. 6,053,965) with the composition of conditioned fuel gas produced by membrane separation using glassy perfluorinated polymer membranes according to the process shown in FIG. 3. The calculations were performed using a modeling program. ChemCad 5.6 (ChemStations, Inc., Houston, Tex.), containing code for the membrane operation developed by MTR's engineering group. Gas feed pressure is assumed to be 325 psia for both the traditional rubbery and glassy perfluorinated membranes; permeate pressure was assumed to be 150 psia and 115 psia for the rubbery and glassy membranes, respectively. Operating temperature was assumed to be room temperature. The same membrane area (200 m$^2$) was assumed to be used for both membrane types.

The results of this comparison are shown in Table 1.

TABLE 1

| Component (vol %)* | Feed Gas (vol %) | Conditioned Fuel Gas (109) (vol %) | Conditioned Fuel Gas (312) (vol %) |
|---|---|---|---|
| Ethane | 4.0 | 2.7 | 2.9 |
| Propane | 9.2 | 4.6 | 3.7 |
| i-Butane | 3.9 | 1.3 | 1.5 |
| n-Butane | 3.9 | 1.3 | 1.5 |
| Pentanes | 1.6 | 0.46 | 0.58 |
| Hexane | 2.8 | 0.55 | 0.78 |
| Total $C_{3+}$ Hydrocarbons | 21.5 | 8.2 | 11.0 |

*Balance is Methane, Carbon Dioxide, and Nitrogen

Stream 109 is the heavy hydrocarbon-depleted residue stream generated using the basic process shown in FIG. 1; stream 312 is the heavy hydrocarbon-depleted permeate stream generated using the process embodiment of the present invention shown in FIG. 3. The fuel gas generated using the process of the invention is on the low pressure permeate end. No recycle needs to be sent to the suction of the compressor, which means the capacity of the compressor is unaffected by our process. This way we are able to produce the same quality fuel gas as in the traditional approach, but the overall compressor horsepower required is lower, as shown in Table 2, below, which is a comparison of the process disclosed in the '965 patent and the process of the present invention.

TABLE 2

|  | '965 Patent | Present Invention |
|---|---|---|
| Total Compressor Horsepower Required | 700 | 600 |
| Conditioned Fuel $C_{2+}$ Content (mol %) | 8.2 | 11.9 |
| Conditioned Fuel Quality Gross Heating Value (Btu/scf) | 1,030 | 1,039 |
| Conditioned Fuel Flow (MMscfd) | 0.20 | 0.20 |

As can be seen from the data shown in Table 2, the process of the present invention requires less compressor horsepower and produces gas having equivalent fuel quality as the gas produced using the prior art process. Both processes produced the same amount of fuel gas (0.2 MMsefd).

Examples 2-5

A set of calculations was performed to show the effect of membrane stage cut (the percentage of the feed gas permeating the membrane). The calculations were modeled on the process scheme of FIG. 2 in conditioning a fuel gas produced by membrane separation using glassy perfluorinated polymer membranes. The calculations were performed using a modeling program, ChemCad 5.6 (ChemStations, Inc., Houston, Tex.), containing code for the membrane operation developed by MTR's engineering group.

Example 2

The calculations were performed assuming a 55% stage cut. The feed stream was assumed to be at a pressure of 660 psia and a temperature of 50° C., and the permeate side of the membranes was assumed to be maintained at 160 psia. The results of the calculations are shown in Table 3. The stream numbers correspond to FIG. 2.

TABLE 3

| Stream | Feed Gas (203) | Residue Stream (206) | Conditioned Fuel Gas (207) |
|---|---|---|---|
| Total kg/h | 8,090 | 3,604 | 4,486 |
| Component (vol %) | | | |
| Methane | 88.4 | 87.7 | 89.0 |
| Ethane | 8.1 | 10.5 | 6.1 |
| Propane | 0.3 | 0.6 | 0.2 |
| Carbon Dioxide | 2.0 | 0.6 | 3.1 |
| Nitrogen | 1.1 | 0.6 | 1.6 |

In this case, operation at a relatively high stage cut increased the methane content of the fuel gas to 89 vol % and reduced the $C_{2+}$ hydrocarbon total content from 8.4 vol % to 6.3 vol %.

Example 3

The calculations were performed assuming a 20% stage cut. The feed stream was assumed to be at a pressure of 810 psia and a temperature of 40° C., and the permeate side of the membranes was assumed to be maintained at 180 psia. The results of the calculations are shown in Table 4. The stream numbers correspond to FIG. 2.

TABLE 4

| Stream | Feed Gas (203) | Residue Stream (206) | Conditioned Fuel Gas (207) |
|---|---|---|---|
| Total kg/h | 1,209 | 986 | 223 |
| Component (vol %) | | | |
| Methane | 80.9 | 79.3 | 87.3 |
| Ethane | 11.2 | 11.9 | 8.3 |
| Propane | 4.0 | 4.6 | 1.4 |
| I-Butane | 1.0 | 1.1 | 0.3 |
| N-Butane | 1.1 | 1.3 | 0.3 |
| Other C5+ | 0.9 | 1.0 | 0.3 |
| Carbon Dioxide | 0.8 | 0.6 | 1.8 |
| Nitrogen | 0.1 | 0.1 | 0.1 |

The model stream in this case had an initial $C_{2+}$ hydrocarbons content of over 18 vol % vol %. The process yielded conditioned fuel gas 207 that is substantially more enriched in methane than feed gas 203. The total $C_{2+}$ hydrocarbon content in this stream is reduced to about 10-11 vol %.

Example 4

The calculations were performed assuming a 40% stage cut. The feed stream was assumed to be at a pressure of 1,000 psia and a temperature of 50° C., and the permeate side of the membranes was assumed to be maintained at 70 psia. The results of the calculations are shown in Table 5. The stream numbers correspond to FIG. 2.

TABLE 5

| Stream | Feed Gas (203) | Residue Stream (206) | Conditioned Fuel Gas (207) |
|---|---|---|---|
| Total kg/h | 6,571 | 4,164 | 2,407 |
| Component (vol %) | | | |
| Methane | 74.6 | 69.3 | 82.5 |
| Ethane | 12.3 | 15.1 | 8.1 |
| Propane | 7.2 | 10.3 | 2.6 |
| I-Butane | 0.7 | 1.2 | 0.1 |
| N-Butane | 1.5 | 2.3 | 0.3 |
| Other C5+ | 0.3 | 0.5 | 0.0 |
| Carbon Dioxide | 2.4 | 0.7 | 4.9 |
| Water | 0.0 | 0.0 | 0.1 |
| Nitrogen | 0.8 | 0.4 | 1.3 |

In this case, the methane content of the fuel gas is raised from about 75 vol % to 83 vol %, and the total $C_{2+}$ hydrocarbon content is reduced from about 22 vol % to about 11 vol %.

Example 5

The calculations were performed assuming an 8% stage cut. The feed stream was assumed to be at a pressure of 128 psia and a temperature of 55° C., and the permeate side of the membranes was assumed to be maintained at 20 psia. The results of the calculations are shown in Table 6. The stream numbers correspond to FIG. 2.

TABLE 6

| Stream | Feed Gas (203) | Residue Stream (206) | Conditioned Fuel Gas (207) |
|---|---|---|---|
| Total kg/h | 1,132 | 1,057 | 74 |
| Component (vol %) | | | |
| Methane | 75.1 | 74.8 | 79.3 |
| Ethane | 7.4 | 7.6 | 4.4 |
| Propane | 6.4 | 6.8 | 2.0 |
| I-Butane | 1.8 | 1.9 | 0.3 |
| N-Butane | 1.8 | 1.9 | 0.3 |
| Other C5+ | 3.6 | 4.0 | 0.3 |
| Carbon Dioxide | 1.3 | 1.0 | 4.8 |
| Water | 1.8 | 1.3 | 7.2 |
| Nitrogen | 0.7 | 0.7 | 1.4 |

In this case, a low stage cut resulted in a conditioned fuel gas 207 in which the total $C_{2+}$ hydrocarbon content is reduced from about 21 volt to only about 7 vol %

We claim:

1. A pro cress for conditioning a portion of a gas stream, the gas stream comprising at least methane and $C_{2+}$ hydrocarbons and the process comprising the following steps:
   (a) withdrawing the portion from the high-pressure gas stream;
   (b) providing a membrane unit having a feed side, a permeate side, and a residue side, and containing a membrane selective for methane over $C_{2+}$ hydrocarbons;
   (c) passing the portion as a feed stream across the feed side under conditions in which transmembrane permeation occurs;
   (d) withdrawing from the residue side a membrane residue stream;
   (e) withdrawing from the permeate side a membrane permeate stream enriched in methane and depleted in $C_{2+}$ hydrocarbons compared with the feed stream; and
   (f) routing the membrane permeate stream as a portion of a fuel gas stream to a fuel user, wherein the process operates at a stage cut of at least 5%.
2. The process of claim 1, wherein the portion is passed to a pre-treatment step before being routed to the membrane unit.
3. The process of claim 2, wherein the pre-treatment step is select d from the group consisting of a filtration step, a heating step, and a combination thereof.
4. The process of claim 1, wherein the membrane residue stream is routed back to the gas stream.
5. The process of claim 4, wherein the membrane residue stream is routed back to the gas stream upstream of where the portion is withdrawn.
6. The process of claim 4, wherein the membrane residue stream is routed back to the gas stream downstream of where the portion is withdrawn.
7. The process of claim 1, wherein the membrane residue stream is partially condensed and recovered as $C_{2+}$ hydrocarbon liquids.
8. The process of claim 1, wherein the fuel user comprises power generation equipment.
9. The process of claim 1, wherein the fuel user is a gas engine.
10. The process of claim 1, wherein the fuel user drives a compressor.
11. The process of claim 10, wherein the gas stream is a high-pressure gas stream created by a compressor driven by a gas engine, and wherein step (f) comprises using the membrane permeate stream as fuel for the gas engine.
12. The process of claim 1, wherein the membrane comprises a polymer having the formula:

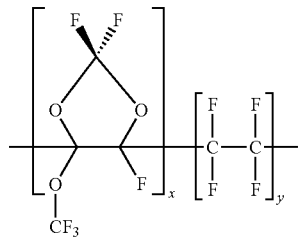

where x and y represent the relative proportions of the dioxo e and the tetrafluoroethylene blocks, such that X+y=1.

13. The process of claim 1, wherein the membrane comprises a polymer having the formula:

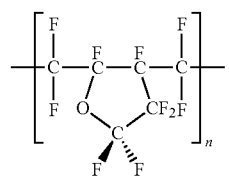

where n is a positive integer.

14. The process of claim 1, wherein the membrane comprises a polymer having the formula:

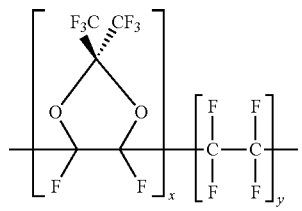

where x and y represent the relative proportions of the dioxole and the tetrafluoroethylene blocks, such that x+y=1.

15. The process of claim 1, wherein the stage cut is at least 8%.

* * * * *